(12) United States Patent
Knippschild et al.

(10) Patent No.: US 9,140,634 B1
(45) Date of Patent: Sep. 22, 2015

(54) HEATING AND MAGNET MODULE FOR A DEVICE FOR THE PURIFICATION OF NUCLEIC ACIDS

(71) Applicant: Analytik Jena AG, Jena (DE)

(72) Inventors: Claus Knippschild, Jena (DE); Claudia Schiessl, Jena (DE)

(73) Assignee: Analytik Jena AG, Jena (DE)

( * ) Notice: Subject to any disclaimer, the term of this patent is extended or adjusted under 35 U.S.C. 154(b) by 0 days.

(21) Appl. No.: 14/480,972

(22) Filed: Sep. 9, 2014

(30) Foreign Application Priority Data

Jun. 27, 2014 (DE) .................... 20 2014 102 945 U

(51) Int. Cl.
| | |
|---|---|
| B01L 7/00 | (2006.01) |
| G01N 1/40 | (2006.01) |
| C12N 15/10 | (2006.01) |
| C12Q 1/68 | (2006.01) |

(52) U.S. Cl.
CPC ... *G01N 1/40* (2013.01); *B01L 7/52* (2013.01); *C12N 15/1003* (2013.01); *C12N 15/1013* (2013.01); *C12Q 1/6806* (2013.01)

(58) Field of Classification Search
CPC .......... C12N 15/1003; C12N 15/1013; C12Q 1/6806; B01L 7/52
USPC ....................................................... 536/25.4
See application file for complete search history.

(56) References Cited

U.S. PATENT DOCUMENTS

| | | | |
|---|---|---|---|
| 6,764,859 B1* | 7/2004 | Kreuwel et al. ............. | 436/178 |
| 2010/0136563 A1* | 6/2010 | Keller et al. .................... | 435/6 |
| 2011/0245483 A1 | 10/2011 | Euting et al. | |

FOREIGN PATENT DOCUMENTS

DE    10 2008 061 714 A1    6/2010

* cited by examiner

*Primary Examiner* — Paul Hyun
(74) *Attorney, Agent, or Firm* — Duane Morris LLP

(57) ABSTRACT

A heating and magnet module for a device for the purpose of purifying nucleic acids, having a plate assembly which has a heating plate, and a magnet carrier plate. The heating plate and the magnet carrier plate can be moved vertically relative to each other between two end positions, in opposition to a spring force. A vessel arrangement is placed on the heating plate, having row or matrix form vessels. One magnet of the magnet carrier plate is functionally assigned to each of these.

10 Claims, 3 Drawing Sheets

US 9,140,634 B1

HEATING AND MAGNET MODULE FOR A DEVICE FOR THE PURIFICATION OF NUCLEIC ACIDS

RELATED APPLICATIONS

The present application claims priority benefit of German Application No. DE 10 2014 102 945.1 filed on Jun. 27, 2014, the contents of which are incorporated by reference in its entirety.

FIELD OF THE INVENTION

Devices for the automatic purification of nucleic acids in biological samples, inside microplates, in principle enable the following technical steps, which are not listed in order of their performance:

synchronous filling of the vessels in a row- or matrix-form vessel arrangement with a reagent or sample liquid, a lysate, an eluate, or magnetic particles in aqueous solution (named "sample liquid" below in each case);

heating of the vessels to warm the sample liquid in the vessels for the purpose of forming a lysate, supporting the elution, or drying the magnetic particles;

addition and/or removal, mixing, and heating of the sample liquid;

deposition of the magnetic particles on the vessel walls by the application of a magnetic field;

washing of the magnetic particles in aqueous solution or reagent fluid by means of mixing, and subsequent purification by means of suctioning off the aqueous residue, and adding a wash solution; and the holding of the vessel arrangement, for example a microplate, on a transport sled in order to prevent the microplate from being pulled off the transport sled when the tips of an automatic pipette device are pulled out of the vessel openings—in this case, wells—wherein said vessel openings can optionally be covered with a film and punctured in advance by means of a sharp-edged auxiliary tool.

BACKGROUND OF THE INVENTION

A device which is suitable for carrying out these steps is frequently also designed for the purpose of placing unused and used vessel arrangements in storage devices (stackers) vertically, removing the same from stackers, and transporting the vessel arrangements between the stackers and individual work spaces. In the process, the vessel arrangements are moved horizontally, for example via transport sleds, and vertically, for example by means of lifters.

The technical features which such a device must have proceed from the technical steps which must be carried out, and which can vary in their sequence and the process parameters thereof.

A device in the class is known from DE 2008 061 714 A1. A device disclosed therein, designed for the use thereof together with multiple vessels ("sample vessels" in the document), has the following features:

a surface for the vessels;

a temperature-controllable device with receptacles for the vessels;

a vessel carrier plate ("sample vessel holder" in the document) with annular magnets, wherein the vessels can be received in the interiors thereof;

a device for the transport of vessel carrier plates from the surface to the temperature-controllable device;

a device for the transfer of liquid from the vessels into other vessels, or into a disposal container; and a control device for controlling the transport device, the device which transfers liquid, and for the controlling the temperature of the temperature-controllable device.

DE 10 20008 061 714 A1, named above, also states that in the prior art a holder has rod-shaped magnets rather than annular magnets, which form a magnetic field working on one side.

From the few details on the device given in DE 10 2008 061 714 A1, it can be clearly derived that a vessel carrier plate equipped with vessels can be connected to the temperature-controllable device to heat the vessels, in such a manner that the vessels can be received by the receptacle of the temperature-controllable device, thereby bringing the vessel carrier plate, and therefore the magnets integrated into the same, into direct contact with the temperature-controllable device, and warming the same as well when the vessels are warmed.

This has the disadvantage that, over the total duration when the vessels are held in the vessel carrier plate—that is, also during a heating of the sample liquid in the vessels, for example to temperatures up to 50° C. for lysing or eluting, or to temperatures up to 40° C. for drying the magnetic particles in the sample vessel—each of the vessels is exposed to a magnetic field and the magnets are warmed at the same time. In this process, the temperature on the heating plate is temporarily more than 40° C. higher than the temperature in the interior of the vessels, due to the dynamically controlled heating profile.

It is not known whether a magnetic field has an effect which influences the lysing process. However, it is known that a plurality of magnetic materials change their magnetic properties when heated. For this reason, according to DE 10 2008 061 714 A1, named above, only selected magnetic materials having a high Curie temperature can be used, which have properties which do not change at these temperatures. To avoid small de-magnetizations, the maximum applied temperature is preferably set a whole step below the Curie temperature. Additional limiting parameters are set by the limited constructed size of the magnets in the heating magnet module, and the coating needed for each magnet, which must allow a thorough cleaning and decontamination, which creates a limitation due to costs in practice in the industry.

A substantial disadvantage of a vessel carrier plate (called a sample vessel holder) according to DE 10 2008 061 714 A1, named above, is the magnetic effect on the vessels, and therefore on the magnetic particles, during the drying of the magnetic particles as well. As a result of the effect of the magnetic field, the magnetic particles are deposited on the vessel walls, stuck to each other, and the magnetic particles must therefore be dried over a longer period of time than if they were loose in the vessel wall. In addition, the action of the magnetic field, together with the evaporation of the liquid, leads to a too-strong agglomeration of the magnetic particles, such that they are much more difficult to homogenize in solution upon the subsequent addition of an aqueous solution.

In actual practice, devices are also known wherein the heating of vessel arrangements, and the insertion thereof into magnetic fields, takes place on work spaces which are separated from each other. In this case, the particularly increased space requirements for two work spaces which are separated spatially is a disadvantage.

SUMMARY OF THE INVENTION

The problem addressed by the invention is that of creating a module for a device for the purpose of purifying nucleic acids, by means of which, on only one work space, a heating of the vessels of a row- or matrix-form vessel arrangement, and the application of magnetic fields to the vessels, can take place with no influence on each other.

This problem is addressed, for a heating and magnetic module for a device for the purpose of purifying nucleic acids, by a vessel arrangement consisting of a vessel carrier plate in which a plurality of vessels are arranged with a grid spacing, in row- or matrix form, a heating plate on which the vessel arrangement is placed, and a plurality of magnets which is determined by the number of vessels. A magnet carrier plate is made, in which the magnets are arranged, depending on the arrangement of the vessels, in such a manner that one magnet is functionally assigned to each vessel at an identical relative position. The heating plate and the magnet carrier plate together form a plate assembly. In this case, the heating plate and the magnet carrier plate are arranged horizontally one above the other, and at least two guide bores are inserted into the heating plate, and the magnet carrier plate has guide rods guided in the guide bores, wherein one coil spring sits between each of the heating plates and the magnet carrier plates such that the heating plate and the magnet carrier plate can be guided vertically relative to each other between a first end position when the coil spring is unloaded, and a second end position when the coil spring is tensioned.

It is advantageous that a guide rail fixed to a frame is included, arranged vertically, wherein the plate assembly is able to move vertically on the same by means of a linear drive, and the heating plate and the magnet carrier plate are able to move vertically with respect to each other on the same. In this case, a limit stop is included above the plate assembly, and is fixed with respect to the guide rail, and the vessel arrangement abuts the limit stop in the second end position of the plate assembly.

It is advantageous if the magnets are bar magnets which are arranged in an identical grid spacing in row or matrix form to that of the vessels in the vessel arrangement, such that one of the bar magnets is specifically functionally assigned to each of the vessels.

As an alternative, the heating plate can have bores arranged in a row or matrix form between each adjacent vessel, with a double grid distance, wherein the magnets are designed as bar magnets and are each embedded in the magnet carrier plate with one end thereof, in the same number as there are bores in the heating plate. Then, the free ends thereof can be inserted into the bores.

The magnets can also advantageously be designed as annular magnets, arranged in a row or matrix form in the same grid spacing as the vessels in the vessel arrangement, such that one of the annular magnets is specifically functionally assigned to each of the vessels.

The heating plate can advantageously have annular bores around the vessels, wherein one of the annular magnets can be inserted into each of the bores.

In order to achieve a particularly good conductance of heat, it is advantageous if the surface shape of the upper side of the heating plate is matched to the base surface of the vessel arrangement.

For the manufacture thereof, it is advantageous if the bores are through-bores, through which the bar magnet can project.

In order to create a defined arrangement of the heating- and magnetic module with respect to an automatic pipette device, it is advantageous if the guide rail and the limit stop have a fixed connection to an automatic pipette device.

It is advantageous if the guide bores have an internal diameter, over a depth which is the same as the length of the maximally compressed coil springs, greater than the outer diameter of the coil springs, such that the magnet carrier plate can be brought to abut directly on the heating plate.

A module according to the invention, also termed a "heating- and magnetic module" below, creates a closed functional unit and exchangeable sub-unit within a device for the purpose of purifying nucleic acids, which has at least one automatic pipette device beyond the module. The automatic pipette device has a pipetting head with a matrix-form arrangement of pipette tips, via which sample liquids can be captured, discharged, and mixed in the wells. The automatic pipette device is fixed in its position, but the pipetting head can move at least vertically, in order to make it possible for the pipette tips to be lowered over, or into, the vessels of a vessel arrangement which is optionally positioned thereunder. The device also advantageously has a transport device for the vessel arrangement in order to position the same horizontally underneath the pipette head.

A vessel arrangement can be a monolithic arrangement of row- or matrix form vessels constructed inside a vessel carrier plate. Microtitration plates, wherein the vessels are termed "wells," and more precisely "deep wells" or "shallow wells," are typical for this arrangement.

The vessel arrangement can also consist of discretely joined vessel carrier plates in which individual vessels stand or sit in holes or blind holes in a row- or matrix form.

Both in a monolithic and in a discrete embodiment of a vessel arrangement, the base surface thereof can be both flat and determined by the shape of the vessels (vessel walls). In the latter case, the vessel walls at least partially project through the vessel carrier plate. Vessel walls can be cylindrical, for example, with flat, conical, or convex base surfaces. Likewise, the vessels as a whole can be, by way of example, in the shape of a spherical segment, a cone, or a truncated cone.

BRIEF DESCRIPTION OF THE DRAWINGS

A heating and magnetic module according to the invention is described in greater detail below with reference to an embodiment and drawings, wherein.

DESCRIPTION OF THE EMBODIMENTS

Figure 1:
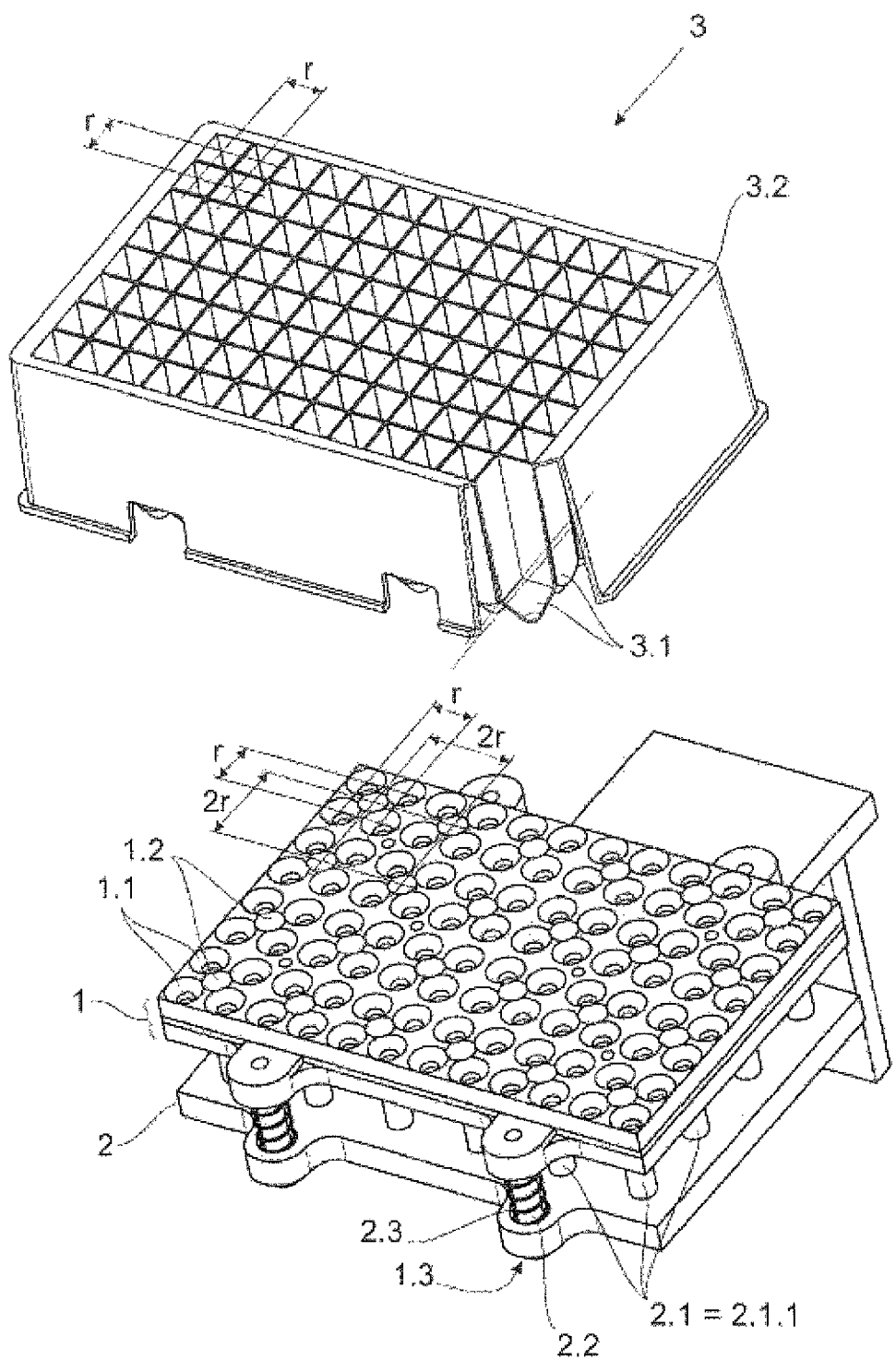
FIG. 1 is an exploded view and shows a plate assembly of a first embodiment of a heating and magnetic module, in a perspective view.

The heating and magnetic module includes a plate assembly with a heating plate 1 and a magnet carrier plate 2 arranged parallel thereto, wherein the heating plate 1 and the magnet carrier plate 2 can be moved between two end positions in opposition to a spring force of coil springs 2.3.

A vessel arrangement 3 is necessary for the description of the design of the plate assembly and the functionality of the heating and magnet module, said vessel arrangement 3 being placed on the heating plate 1 in a defined manner, for the proper functioning of the heating and magnet module, for which reason the vessel arrangement 3 is described as belonging to the heating and magnet module.

The defined placement of the vessel arrangement 3 can be performed by including bumps on the heating plate 1 which delimit the periphery of the vessel arrangement 3, wherein the vessel arrangement 3 is placed between these. However, the defined placement preferably is performed by the heating plate 1 having a surface shape which is matched to a base surface of the vessel arrangement 3, wherein the vessel arrangement 3 is inserted into this surface shape. In this way, a higher surface contact area is also advantageously created between the vessel arrangement 3 and the heating plate 1.

A heating and magnet module according to the invention is in a first end position, corresponding to a standby position, when the coil springs 2.3 are unloaded and the heating plate 1 and the magnet carrier plate 2 have a maximum possible distance from each other. In this case, the inherent weight of the filled and positioned vessel arrangement 3, which already in itself results in a minimal pre-tensioning of the coil springs 2.3, should be ignored in this case.

For the purpose of heating vessels 3.1 of the vessel arrangement 3, the heating plate 1 is pressed against the vessel arrangement 3, wherein the distance between the magnet carrier plate 2 and the heating plate 1 should remain as large as possible. For this purpose, either the heating plate 1 is moved toward the magnet carrier plate 2, which is then stationary, by means of a predetermined force, or the magnet carrier plate 2 is moved toward the heating plate 1, which is then stationary, by means of a predetermined force. The coil springs 2.3 are pre-tensioned in a defined manner, and the return force of the coil springs 2.3 generated as a result of a pressing force between the vessel arrangement 3 and the heating plate 1. The heating plate 1 and the magnet carrier plate 2 are now in an intermediate position which corresponds to the heating position.

In order to achieve a magnetic field effect on the vessel 3.1, the distance between the heating plate 1 and the magnet carrier plate 2 is reduced to a minimum. For this purpose, either the heating plate 1 is once again moved toward the magnet carrier plate 2, which is then stationary, or the magnet carrier plate 2 is moved toward the heating plate 1, which is then stationary. The coil springs 2.3 are maximally tensioned, and the distance between the heating plate 1 and the magnet carrier plate 2 is thereby reduced to a minimum. The heating plate 1 and the magnet carrier plate 2 are now in a second end position which corresponds to the separation position.

Microplates are preferably used as the vessel arrangement 3. They have standard external dimensions and differ among themselves by the number of wells, and therefore the grid spacing between two adjacent wells. Microplates with 24 or 96 wells are typical for applications of a device for purifying nucleic acids.

A heating- and magnet module according to the invention is described below with reference to a preferred embodiment.

In addition to the plate assembly named above, having the vessel arrangement 3 positioned, which in this case is a microplate, the heating- and magnet module has a guide rail 4 fixed to a frame and arranged vertically, a linear drive 5 for the purpose of moving the plate assembly along the guide rail 4, and a limit stop 6 which is fixed with respect to the guide rail 4, on which the plate assembly can be brought to a stop.

The plate assembly shown in FIG. 1 is designed, by way of example, for use together with a so-called 96-er microplate, having twelve wells in the rows and eight wells in the columns. A magnet 2.1, constructed in this case as a bar magnet 2.1.1, is inserted between each group of four adjacent wells, underneath the microplate in a magnet carrier plate 2—which is described in greater detail below—in such a manner that twenty-four bar magnets 2.1.1 are included in this embodiment. This means that exactly one bar magnet 2.1.1 is functionally assigned to each well, and the bar magnets 2.1.1 are functionally assigned to two wells in an edge region, and four wells in an inner region. The relative position of the bar magnets 2.1.1 to a well in each case is identical.

In the same way that the number and the arrangement of the pipette tips of the automatic pipette device are matched to the use of a microplate with an accordingly identical number and arrangement of wells, the heating- and magnet module is also accordingly matched as regards its size and the number of bar magnets 2.1.1.

The heating plate 1 is a heatable flat plate with peripheral dimensions and a surface shape which are matched to the outer dimensions of the microplate. It is at least large enough that the positioned microplate does no project beyond the heating plate 1. The surface shape of the upper side of the heating plate 1 is matched to the base surface of the microplate in such a manner that the individual wells have the greatest possible surface contact area with the heating plate 1. The surface shape of the upper side of the heating plate 1 preferably corresponds to the negative of the microplate, such that the wells are embedded in the heating plate 1. The upper side of the heating plate 1 therefore has a matrix-form arrangement of depressions 1.1 designed in columns and rows, corresponding to the wells of the microplate.

The heating plate 1 is constructed of a material with good heat conducting properties, which is non-magnetic or [non-]magnetizable, and preferably can be easily machined, such as aluminum.

Electric heating coils, by way of example, are integrated into the heating plate 1 for the purpose of heating the same, or the heating plate 1 has a heating film attached to the underside thereof. The heating plate 1 has an arrangement of bores 1.2, which are essential to the invention, wherein one hole is found between each of four adjacent depressions 1.1. The bores 1.2 are preferably through-bores. They serve the purpose of temporarily receiving bar magnets 2.1.1 of the magnet carrier plate 2, which are preferably able to project through the bores 1.2. Moreover, preferably four, and in any case at least two, guide bores 1.3 are included in the heating plate 1, enabling—together with the guide rods 2.2—a guided, relative movement of the heating plate 1 and the magnet carrier plate 2 with respect to each other, with one translational degree of freedom.

The magnet carrier plate 2 is likewise a flat plate, preferably having the same peripheral contour and peripheral size as the heating plate 1. Bar magnets 2.1.1 are embedded into the magnet carrier plate 2, each by one of their ends, with the same grid spacing as the bores 1.2 present in the heating plate 1. The number of the bores 1.2 corresponds to the number of the wells, operated by magnets, of the microplates in the present application. Four guide rods 2.2 are arranged beyond the bores 1.2, in the magnet carrier plate 2, which engage in four guide bores 1.3 of the heating plate 1 arranged above the magnet carrier plate 2. The axes of the guide rods 2.2 and the guide bores 1.3 run perpendicular to the surfaces of the heating plate 1 and the magnet carrier plate 2, such that these can be moved toward each other and away from each other, guided in the direction of their surface normal. Coil springs 2.3 sit on the guide rods 2.2, coaxial thereto and having the same dimensions, each capable of generating a spring force—also termed a return force—in the direction of the axes of the guide rods 2.2.

For the purpose of operating the heating- and magnet module, the guide rail 4 is arranged standing vertically, whereby the heating plate 1 and the magnet carrier plate 2 are oriented horizontally, and are likewise able to be moved vertically toward each other. The plate assembly is mounted vertically above the magnet carrier plate 2 on the guide rail 4 in a manner allowing movement, wherein the heating plate 1 and the magnet carrier plate 2 can be moved toward each other between the first and the second end position.

Figure 2A:
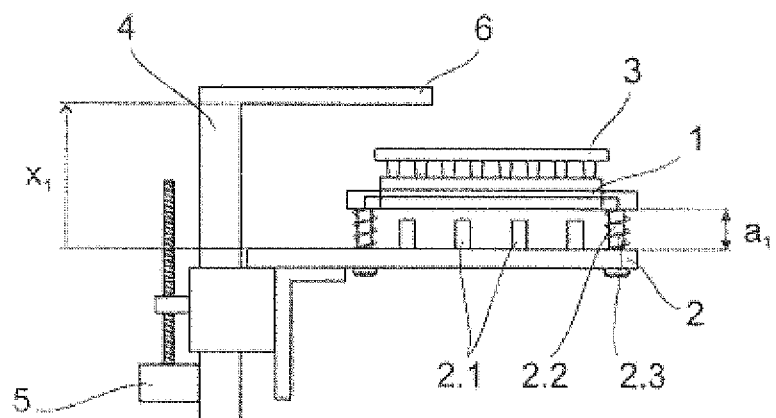
FIG. 2a shows a principle sketch of a first embodiment of a heating and magnetic module in the first end position.

In the first end position, the module is in the standby position (FIG. 2a).

The coil springs 2.3 are in a state of tension created only by the weight of the heating plate 1 and the microplate, and this state is ignored in the following considerations. The heating plate 1 and the magnet carrier plate 2 have the greatest possible, first spacing $a_1$ from each other, and the magnet carrier plate 2 is arranged at a first distance $x_1$ from the limit stop 6—which is greater than the sum of the first spacing $a_1$ and the thickness of the heating plate 1 and the height of the microplate.

Figure 2B:
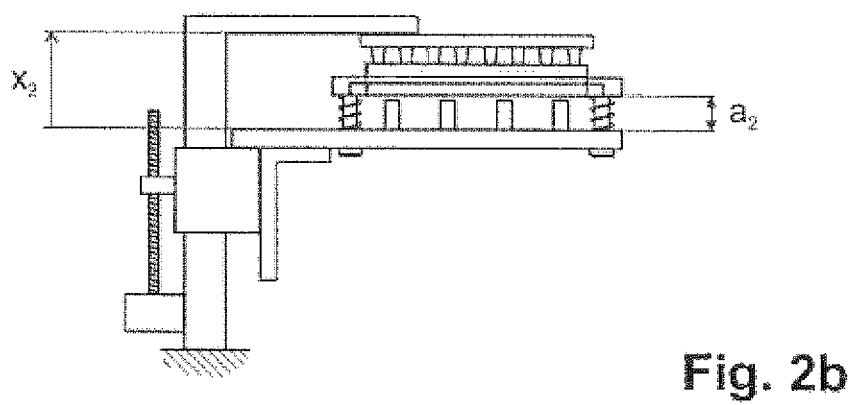
FIG. 2b shows a principle sketch of a first embodiment of a heating and magnetic module in the intermediate position.

By means of the linear drive 5, the plate assembly is lifted along the guide rail 4. Until the microplate comes to abut the limit stop 6, the first spacing $a_1$ is maintained. With a further lifting of the plate assembly, the microplate remains on the limit stop 6 and the coil springs 2.3 are increasingly compressed and therefore tensioned, while the first spacing $a_1$ is reduced to a second spacing $a_2$ in which the coil springs 2.3 are pre-tensioned. The pretensioning produces a spring force in each of the coil springs 2.3, which functions as a pressing force between the heating plate 1 and the microplate. The heating- and magnet module is now in an intermediate position which constitutes a first working position and corresponds to the heating position (see FIG. 2b).

In contrast to the devices in the class, wherein a microplate lies on a heating plate only with its own weight, to be heated, in the present case the force-fit contact, which optionally leads to a positive fit for the purpose of removing any play, improves the heat conductance and therefore the energy efficiency of the heating plate.

The magnet carrier plate 2 is in the heating position at a second distance $x_2$ from the limit stop 6, which is the same as the sum of the second spacing $a_2$ and the thickness of the heating plate 1 and the height of the microplate. The second spacing $a_2$ is sufficiently large such that the bar magnets 2.1.1 are still entirely outside of the heating plate 1. As a result, they are neither heated by the heating plate 1 nor is the magnetic field produced by each of the bar magnets 2.1.1 applied to the microplate.

At this point, the heating plate 1, in the heating position, can be switched on, and the microplate and the sample liquid in the same can be heated. In addition, in the heating position, when the heating plate 1 is preferably switched off or in the standby position, the microplate can, first of all, be held so that the force of the tips of an automatic pipette device, being pulled out, is opposed, said force resulting from contact with the edges of the sealing openings (the openings which are created in a film, using a sharp-edged auxiliary tool, the film serving the purpose of covering the wells), which otherwise leads to a slight lifting of the microplates if the same are positioned loosely on the horizontal transport sled, and, secondly, can be filled or emptied. The sample liquid can also be mixed in each of the wells by a pipette head arranged above the microplate being lifted and lowered. The heating of the microplate is carried out, by way of example, for the purpose of forming a lysate from the biological sample, for the purpose of supporting the elution if an eluate is being produced, or for the purpose of drying magnetic particles present in the wells, the same optionally being loose in the wells outside of an application of a magnetic field from the bar magnets.

Figure 2C:
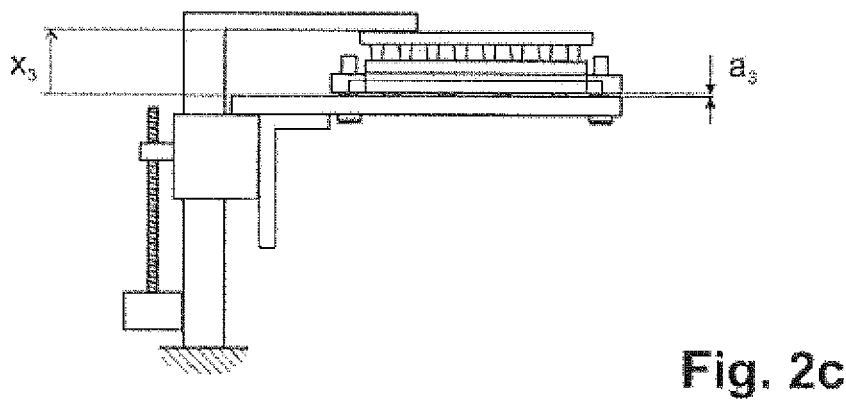
FIG. 2c shows a principle sketch of a first embodiment of a heating and magnetic module in the second end position.

A second end position (see FIG. 2c) which constitutes a second working position and corresponds to the separation position, is assumed by the heating- and magnet module after the magnet carrier plate 2 has been further moved upward on the guide rail 4 by means of the linear drive 5, far enough that the coil springs 2.3 are preferably completely compressed, and the bar magnets 2.1.1 are thereby inserted to the maximum inside the heating plate 1. The magnet carrier plate 2 now has the smallest possible, third, spacing $a_3$ from the heating plate 1, which corresponds to, at most, the length of the compressed coil springs 2.3. It can go down to zero if the guide bores 1.3 extend over a depth which is equal to the length of the compressed coil springs 2.3, such that the same can be completely compressed in the guide bores 1.3. The magnet carrier plate 2 then has a third distance $x_3$ from the limit stop, which is only determined by the thickness of the heating plate 1, the height of the microplate, and, at most, the length of the completely compressed coil springs 2.3. The magnetic fields of the bar magnets 2.1.1 now are applied to their greatest extent to the microplate, and therefore optionally to the magnetic particles in the wells. The magnetic particles are attracted by the bar magnets 2.1.1 and are deposited on the well walls of the wells. By means of a pipette head arranged above the microplate, the aqueous solution can be suctioned out of the wells in a so-called separation step, without the pipette tips of the pipette head taking the magnetic particles as well. The heating plate 1 remains switched off during this process step.

A substantial advantage of a heating- and magnet module according to the invention is that, with the positioning of the heating- and magnet module underneath a pipette head, the heating plate 1 and the magnet carrier plate 2 are arranged on the same work space, and the work steps of heating and separation can be carried out without the magnetic fields, needed for separation, being applied to the microplate during the heating thereof.

In the heating position, the bar magnets 2.1.1 are outside of and distanced from the heating plate 1, and are therefore not heated together with the heating plate 1 during the heating thereof, and therefore of a microplate lying on the same.

In the separation position, the bar magnets 2.1.1 are inside the heating plate 1, and therefore form their magnetic fields around the wells, By selecting a low heat conductivity coefficient of the heating plate 1, only a minimum residual heat of the same remains following a heating step. As a result, this has no significant influence on the bar magnets 2.1.1.

The heating and magnet module advantageously comes out by means of only one linear drive 5.

A heating and magnet module is sensibly used in a fixed arrangement to an automatic pipette device, wherein the guide rails 4 and the limit stop 6 can be components of the automatic pipette device.

The limit stop 6 can be designed as a frame or can be formed by bolts on which the microplate comes to rest along one edge therefore abutting its periphery. The microplate can also be capable of being fixed with respect to the guide rail 4 after being placed on the heating plate 1, and then itself can offer a limit stop surface, so that the additional limit stop 6 can be dispensed with.

Figure 3:
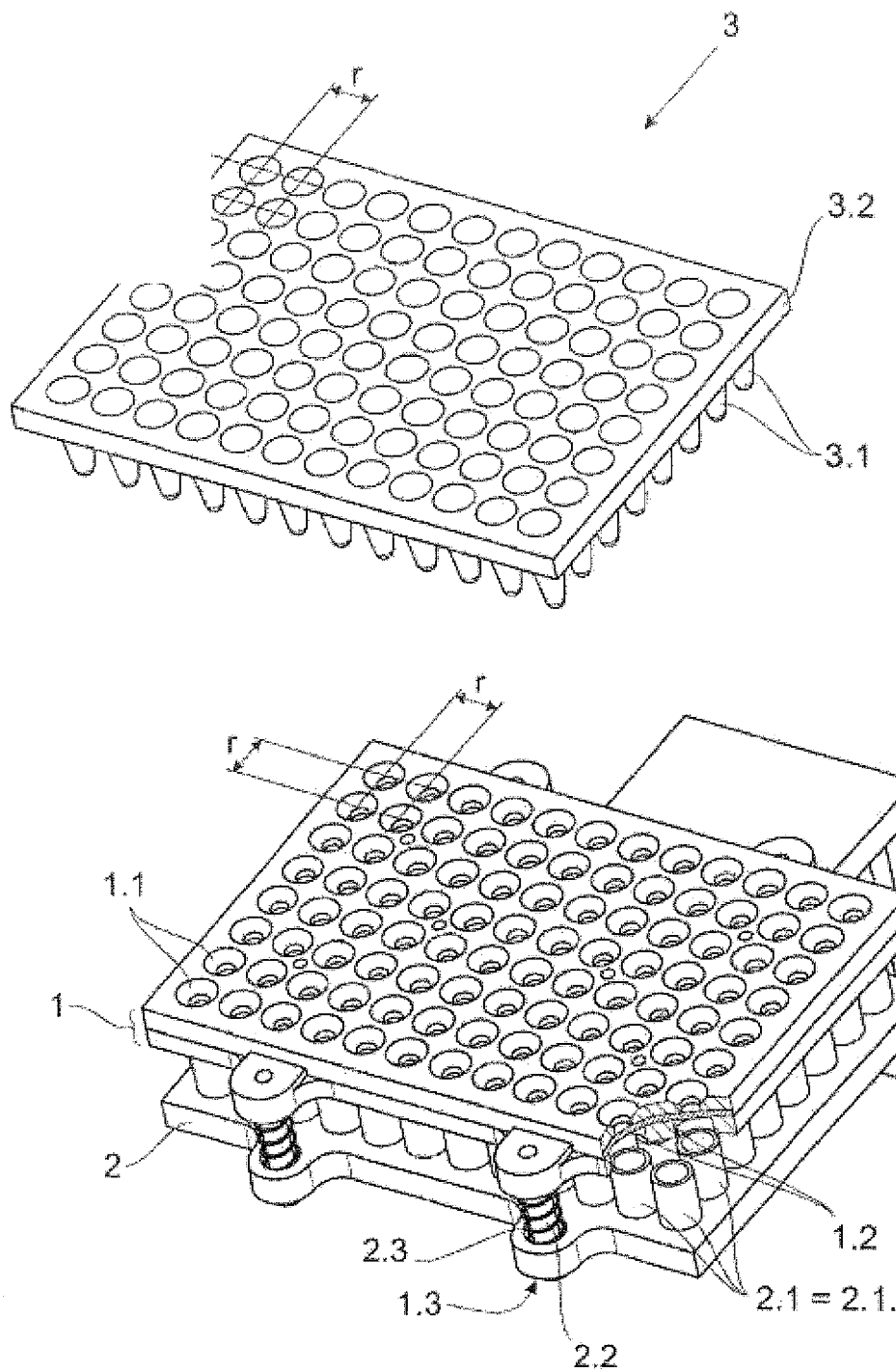
FIG. 3 is an exploded view and shows a plate assembly of a second embodiment of a heating and magnetic module in a perspective view.

A second embodiment, shown in FIG. 3, differs from the first embodiment only in that the magnets 2.1 are not designed as bar magnets 2.1.1, but rather as annular magnets 2.1.2. In this case, the bores 1.2 are annular blind holes, each arranged around a vessel 3.1, such that one annular magnet 2.1.2 is functionally assigned to each vessel 3.1, and one vessel 3.1 is functionally assigned to each annular magnet 2.1.2. Such a functional assignment is termed a discrete assignment. The magnetic particles in this embodiment are advantageously deposited distributed around the vessel walls of the vessels 3.1. However, one ring magnet 2.1.2 can also be functionally assigned to only every second vessel 3.1.

In a third, fourth, and fifth embodiment (not shown), there are not bores 1.2 in the heating plate 1 into which the bar magnets 2.1.1 and/or the annular magnets 2.1.2 are inserted. The annular magnets 2.1.2 and/or the bar magnets 2.1.1, which in this case can also be arranged in the same row- or matrix form arrangement, and with the same grid spacing r, as the vessels 3.1, then do not penetrate into the heating plate 1. Rather, they only approach the heating plate 1. This can be sufficient, given accordingly strong magnets 2.1, and reduces the complexity of manufacture. These embodiments are then particularly advantageous if the vessel arrangement 3 has a flat base surface. The magnets 2.1 can be completely embedded in the magnet carrier plate 2, or can project out of the same as in the first two embodiments.

Additional embodiments should differ from the embodiments named above in that the magnet carrier plate 2 is arranged fixed to a frame, and means are included for the purpose of lowering the heating plate 1 to the magnet carrier plate 2. In this case, as in the previous embodiments, bores 1.2 can be configured in the heating plate 1 in order for the magnets 2.1 to be inserted. However, it is also possible to not include any.

The means for lowering the heating plate 1 to the magnet carrier plate 2, in opposition to the spring forces of the coil springs 2.3, can likewise be a linear drive 5 which guides a limit stop 6 against the vessel arrangement 3, and then guides the vessel arrangement 3, carrying the heating plate 1 with it, toward the magnet carrier plate 2. The limit stop 6 can be guided on a guide rail 4 arranged vertically.

The means for lowering can also be a separate unit of a device, for example a lifter, which otherwise is used to lower vessel arrangements 3, particularly microplates, onto transport devices, or to place the same in stackers.

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

LIST OF REFERENCE NUMBERS 1 heating plate
1.1 depression
1.2 bores
1.3 guide bores
2 magnet carrier plate
2.1 magnet
2.1.1 bar magnet
2.1.2 annular magnet
2.2 guide rod
2.3 coil spring
3 vessel arrangement
3.1 vessel
3.2 vessel carrier plate
4 guide rail
5 linear drive
6 limit stop
r grid spacing
$a_1$ first spacing
$a_2$ second spacing
$a_3$ third spacing
$x_1$ first distance
$x_2$ second distance
$x_3$ third distance

What is claimed is:

1. A heating and magnetic module for a device for the purpose of purifying nucleic acids, comprising a vessel arrangement, said arrangement having a vessel carrier plate, a plurality of vessels arranged in said vessel carrier in a row or matrix form, with a grid spacing, a heating plate on which said vessel arrangement is placed, and a plurality of magnets, said plurality of magnets being determined by the number of the vessels, a magnet carrier plate in which said magnets are arranged in such a manner that one magnet is functionally assigned to each vessel in an identical relative position, and that said heating plate and the magnet carrier plate, forming a plate assembly together, are arranged one above the other, when in a horizontal orientation, and at least two guide bores being inserted into said heating plate, said magnet carrier plate having guide rods which are guided into said guide bores, wherein a coil spring sits on each guide rod between the heating plate and the magnet carrier plate, such that the heating plate and the magnet carrier plate can be guided vertically relative to each other between a first end position, wherein the coil springs are unloaded, and a second end position, wherein the coil springs are tensioned.

2. A heating and magnetic module according to claim 1, further comprising a guide rail fixed to a frame and arranged vertically, wherein said plate assembly can be moved vertically thereon by means of a linear drive, and wherein the heating plate and the magnet carrier plate can be moved vertically thereon with respect to each other, and further comprising a limit stop arranged above said plate assembly fixed relative to the guide rail, said vessel arrangement abutting said limit stop in the second end position of the plate assembly.

3. A heating and magnetic module according to claim 2, wherein said guide rail and the limit stop have a fixed connection to an automatic pipette device.

4. A heating and magnetic module according to claim 2, wherein said guide bores have an internal diameter, over a depth which is the same as a length of the maximally compressed coil springs, greater than the outer diameter of the coil springs, such that the magnet carrier plate can be brought to abut directly on the heating plate.

5. A heating and magnetic module according to claim 1, wherein said magnets are bar magnets which are arranged in a row or matrix form with the same grid spacing as the vessels in the vessel arrangement, such that each of the bar magnets is functionally assigned specifically to one of the vessels.

6. A heating and magnetic module according to claim 1, further comprising bores arranged in said heating plate in a row or matrix form with a double grid spacing between each pair of adjacent vessels, and wherein said magnets are bar magnets which are each embedded in the magnet carrier plate by one end thereof, in the same number as there are bores in the heating plate, wherein the same are inserted into the bores by their free ends.

7. A heating and magnetic module according to claim 6, wherein said bores are through-bores through which said bar magnets can project.

8. A heating and magnetic module according to claim 1, wherein said magnets are annular magnets which are arranged in a row or matrix form with the same grid spacing as the vessels in the vessel arrangement, such that each of the annular magnets is functionally assigned specifically to one of the vessels.

9. A heating and magnetic module according to claim 1, wherein said magnets are annular magnets which are arranged in a row or matrix form with the same grid spacing as the vessels, such that each of the annular magnets is functionally assigned specifically to one of the vessels, and in that the heating plate has annular bores around the vessels, wherein one annular magnet can be inserted into each of the same.

10. A heating and magnetic module according to claim 1, wherein the surface shape of an upper side of the heating plate is matched to a base surface of the vessel arrangement.

* * * * *